United States Patent
Chung et al.

(10) Patent No.: US 8,211,453 B2
(45) Date of Patent: *Jul. 3, 2012

(54) ANTIBACTERIAL COMPOSITION CONTAINING ORGANIC SILVER COMPLEXES, ANTIBACTERIAL TREATMENT METHODS USING THE SAME AND ANTIBACTERIAL FORMED ARTICLE

(75) Inventors: Kwang-Choon Chung, Gyeonggi-do (KR); Hyun-Nam Cho, Gyeonggi-do (KR); Eun-Jin Park, Seoul (KR); Young-Kwan Seo, Gyeonggi-do (KR); Ju-Jin Choi, Gyeonggi-do (KR); Dong-Lib Kim, Gyeonggi-do (KR); Hyoung-Seok Kim, Daejeon (KR)

(73) Assignee: Inktec Co., Ltd., Kyeongki-do (KR)

( * ) Notice: Subject to any disclaimer, the term of this patent is extended or adjusted under 35 U.S.C. 154(b) by 514 days.

This patent is subject to a terminal disclaimer.

(21) Appl. No.: 12/282,982

(22) PCT Filed: Mar. 14, 2007

(86) PCT No.: PCT/KR2007/001255
§ 371 (c)(1),
(2), (4) Date: Feb. 23, 2009

(87) PCT Pub. No.: WO2007/105912
PCT Pub. Date: Sep. 20, 2007

(65) Prior Publication Data
US 2009/0324739 A1    Dec. 31, 2009

(30) Foreign Application Priority Data
Mar. 14, 2006 (KR) .................. 10-2006-0023735

(51) Int. Cl.
*A61K 33/38* (2006.01)
*A01N 25/00* (2006.01)
*A01N 25/02* (2006.01)
*A01N 47/10* (2006.01)
*A01N 37/00* (2006.01)
*A01N 33/00* (2006.01)
*A01N 33/12* (2006.01)
*A01N 59/16* (2006.01)
*A61K 31/14* (2006.01)

(52) U.S. Cl. ........ 424/405; 424/618; 514/506; 514/579; 514/642

(58) Field of Classification Search ........... 424/405, 424/618
See application file for complete search history.

(56) References Cited

U.S. PATENT DOCUMENTS

| | | |
|---|---|---|
| 3,979,382 A | 9/1976 | Martinez-Alvarez et al. |
| 4,542,214 A | 9/1985 | Bechara |
| 4,652,465 A | 3/1987 | Koto et al. |
| 6,387,542 B1 * | 5/2002 | Kozlov et al. ............ 428/673 |
| 2002/0117652 A1 * | 8/2002 | Sano et al. .............. 252/500 |

FOREIGN PATENT DOCUMENTS

| | | |
|---|---|---|
| JP | 2002293705 A | 10/2002 |
| JP | 1020060011083 A | 2/2006 |
| KR | 1020040003451 A | 1/2004 |
| KR | 1020040048560 A | 6/2004 |
| KR | 1020050075905 A | 7/2005 |
| KR | 1020050121149 A | 12/2005 |
| WO | 2004085165 A1 | 10/2004 |
| WO | WO 2006093398 * | 9/2006 |

OTHER PUBLICATIONS

Abstract of JP61163975 published Jul. 24, 1986; 5 pages.*

* cited by examiner

*Primary Examiner* — Ernst Arnold
(74) *Attorney, Agent, or Firm* — The Webb Law Firm

(57) ABSTRACT

The present invention relates to antibacterial composition containing silver complexes, antibacterial treatment methods using the same and antibacterial formed article, in which the antibacterial composition containing silver complexes is economical, not wearing off due to washing, cleaning, rubbing, etc., firmly combined to improve durability and antibacterial effect, and applicable to various products due to great solubility and stability.

13 Claims, 4 Drawing Sheets

[Fig.1]
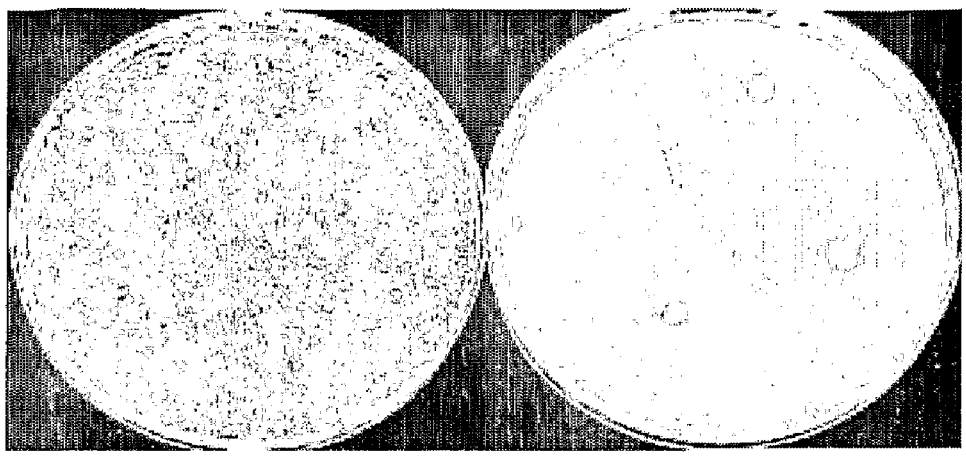
(a)      (b)
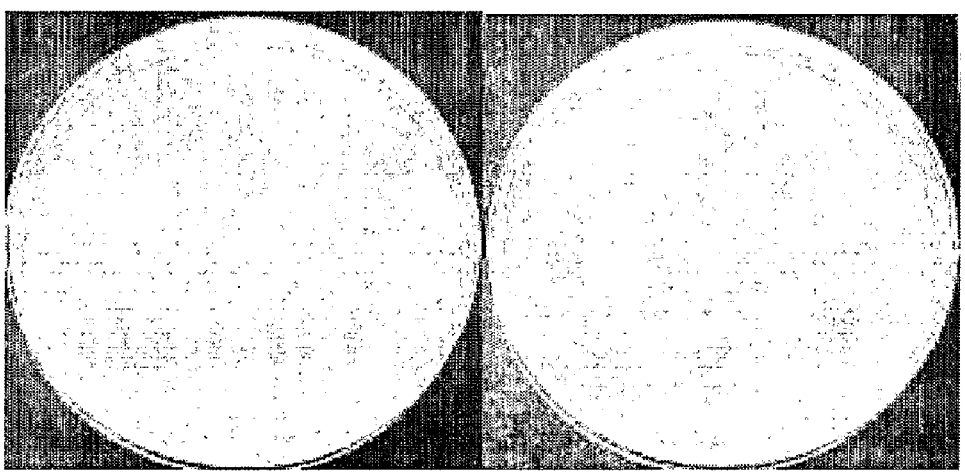
(c)      (d)
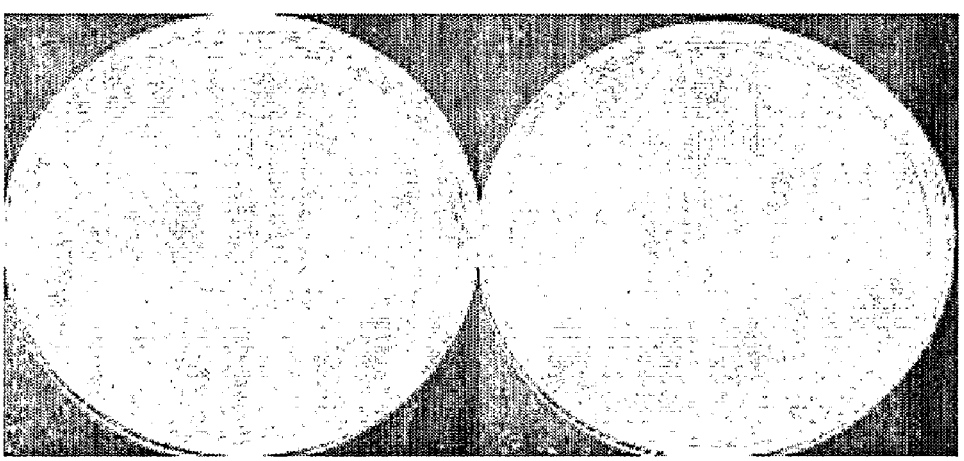
(e)      (f)

[Fig.2]
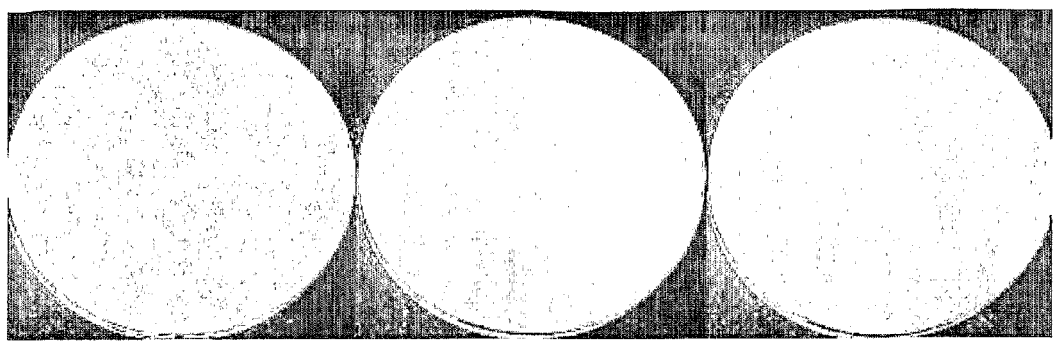
(a) (b) (c)
[Fig.3]
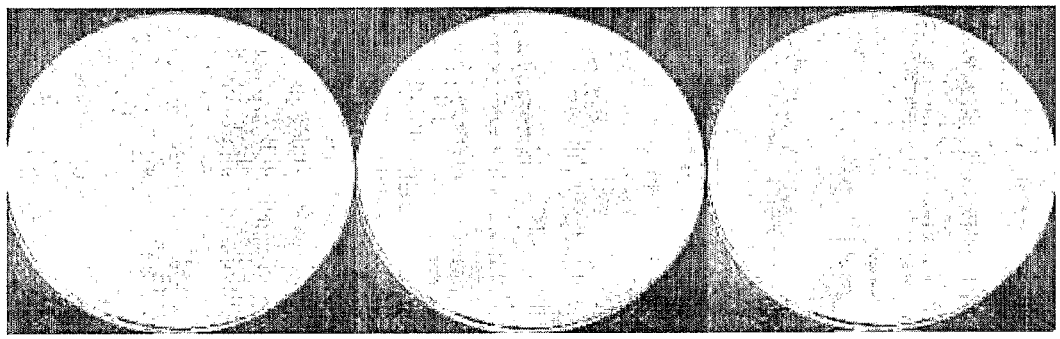
(a) (b) (c)

[Fig.4]
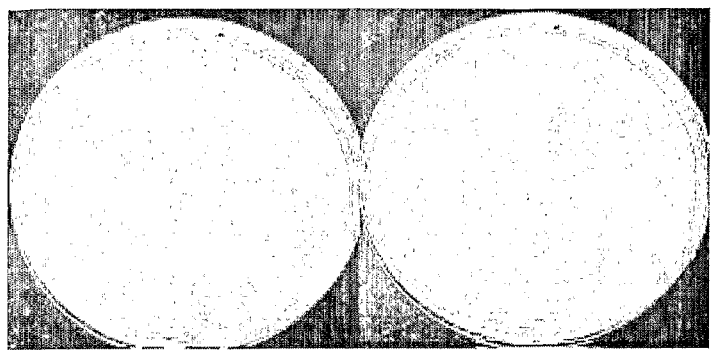
(a)     (b)
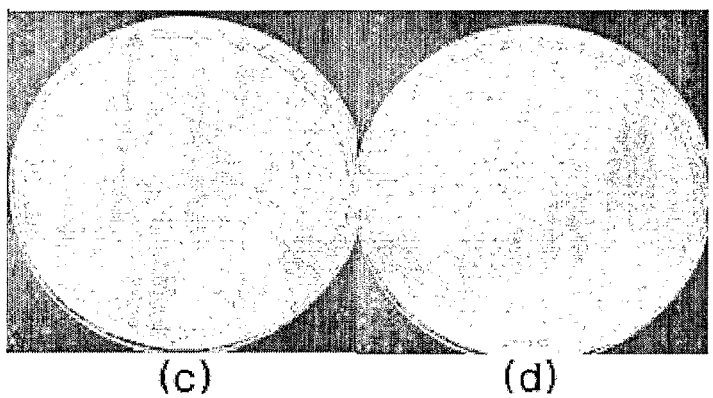
(c)     (d)
[Fig.5]
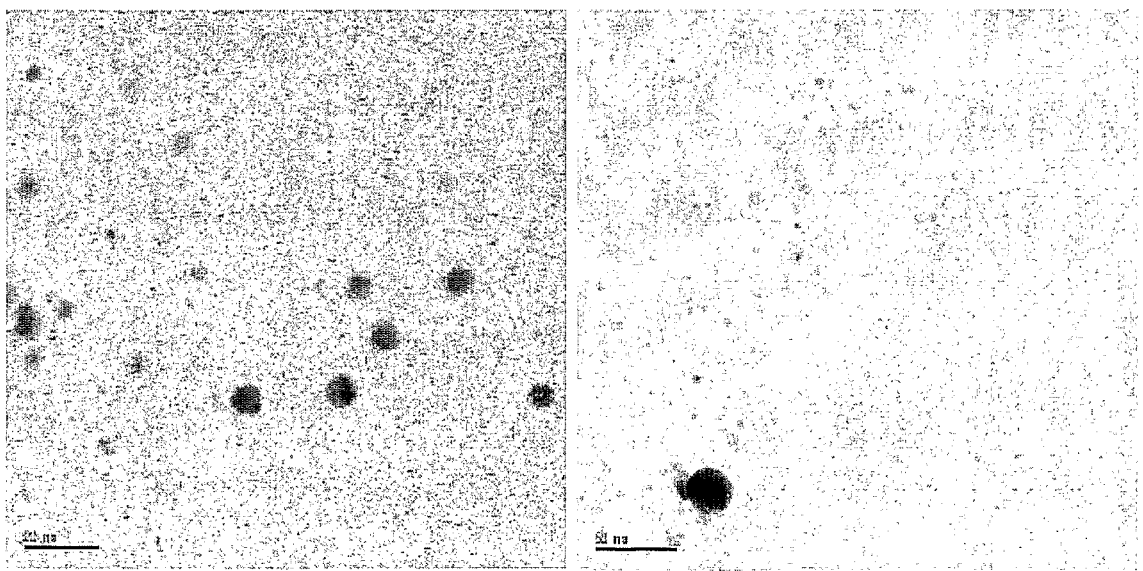
(a)     (b)

[Fig.6]
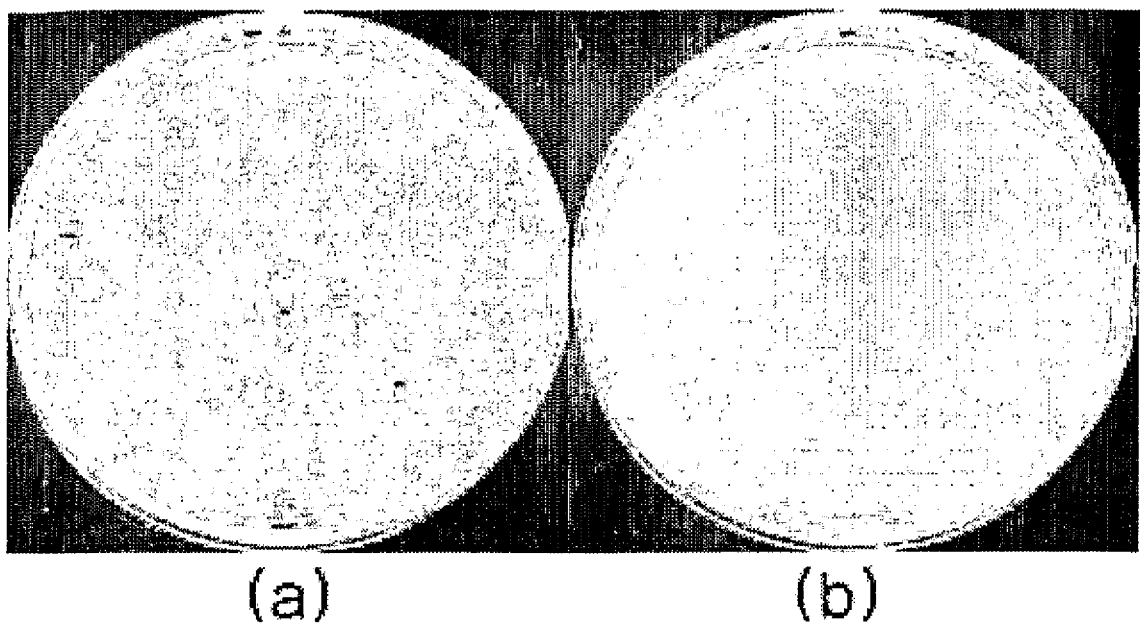
(a)  (b)

ANTIBACTERIAL COMPOSITION CONTAINING ORGANIC SILVER COMPLEXES, ANTIBACTERIAL TREATMENT METHODS USING THE SAME AND ANTIBACTERIAL FORMED ARTICLE

TECHNICAL FIELD

The present invention relates to antibacterial composition containing silver complexes, antibacterial treatment methods using the same and antibacterial formed article.

BACKGROUND ART

Generally, silver (Ag) is known as possessing the antibacterial effect that kills approximately 650 bacteria by stirring up the electron transfer system in the cell membranes outside the bacteria's body, so it is unlikely to create resistant bacteria. Also, since it is not poisonous to human body unlike common organic antibacterial agents, it is applied to many antibacterial agents and other materials using silver.

The demand for antibacterial materials is on the rise as economy booms, the quality of life continues to improve, and consumers pursue healthy and pleasant life. Recently, antibacterial manufacturing has been applied to a variety of textiles from clothing, bedding, interior goods to antibacterial filters, medical textile products, and even to wallpapers, floors, tableware, washing machine, etc. And its application range is getting bigger now.

Korean Laid-Open Patent Publication No. 2004-0003451 discloses the antibacterial agents in which 0.3~20 nm of silver colloidal particles are dispersed on the concentration of 0.5~50 ppm. Also, Korean Laid-Open Patent Publication No. 2005-0075905 discloses how to prepare antibacterial functional complex textiles through 20~70 nm sized silver particles that are dispersed within the island component of a sea-island typed conjugate fiber and then chemically eluted, so that the silver particles can remain on the surface of the fiber. Also, Japanese Laid-Open Patent Publication No. PYUNG2002-293705 discloses the silvery antibacterial agents composed of inorganic adsorbents in which silver colloidal particles and cationic surfactants are embedded.

Korean Laid-Open Patent Publication No. 2005-0121149 discloses how to make antibacterial ceramic products by adding the nanosilver antibacterial agent to the glaze or spraying it on the surface of ceramic products, which are then fired.

However, the former silver antibacterial agent made by precedent technology has a few problems that prohibit it from being used for various products.

Firstly, it is hard to apply silver particles to antibacterial products. For instance, in a trial of fixing silver particles onto the textile surface, the particles are not firmly stuck to it but eventually wearing off due to washing, rubbing, etc., which makes the antibacterial effect deteriorate. When adhesives or resins are used to make up for the weakness, they also fail to induce antibacterial effects from silver, since the silver particles exist inside the adhesives.

Secondly, the nano-sized silver particles are expensive. Although silver has great disinfection power for the size smaller than nano-size, it is uneconomical to be industrialized due to the high cost.

Thirdly, the silver colloidal antibacterial agents which silver particles are dispersed should go through the process where silver particles are uniformly dispersed in solvents. By such dispersion process, the manufacturing cost becomes high and the product stability drops.

DISCLOSURE

Technical Problem

An object of the present invention is to provide the antibacterial composition containing silver complexes, which is economical, not wearing off due to washing, cleaning, rubbing, etc., firmly combined to improve durability and antibacterial effect, and applicable to various products due to great solubility and stability to solve all the problems above.

Another object of the present invention is to provide the antibacterial treatment methods using the antibacterial composition containing silver complexes above.

Another object of the present invention is to provide the antibacterial formed articles processed by the antibacterial treatment methods using the antibacterial composition containing silver complexes above.

Technical Solution

To achieve such objects, the present invention provides the antibacterial composition containing silver complexes that are obtained by the reaction between the silver compound (Formula 1) and ammonium carbamate or ammonium carbonate based compounds (Formula 2 to 4).

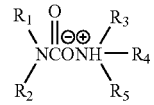

[Formula 1]

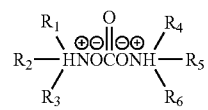

[Formula 2]

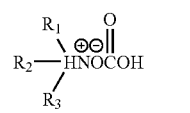

[Formula 3]

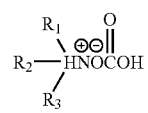

[Formula 4]

[In the formula above,

X is a substituted group selected from the group consisting of oxygen, sulfur, halogen, cyano, cyanate, carbonate, nitrate, nitrite, sulfate, phosphate, thiocyanate, chlorate, perchlorate, tetrafluoro borate, acetylacetonate, carboxylate and their derivatives, n is an integer of 1~4, $R_1$ to $R_6$ are substituted groups independently selected from the group consisting of hydrogen, C1-C30 of aliphatic or cycloaliphatic alkyl group or aryl or aralkyl group, alkyl and aryl group substituted with functional group, heterocyclic compound, polymer compound and their derivatives.]

In the formula 1 above, n is an integer of 1~4, X is a substituted group selected from the group consisting of oxygen, sulfur, halogen, cyano, cyanate, carbonate, nitrate, nitrite, sulfate, phosphate, thiocyanate, chlorate, perchlorate, tetrafluoro borate, acetylacetonate, carboxylate and their derivatives, for example, silver oxide, silver thiocyanate, silver sulfide, silver chloride, silver cyanide, silver cyanate, silver carbonate, silver nitrate, silver nitrite, silver sulfate, silver phosphate, silver perchlorate, silver tetrafluoro borate, silver acetylacetonate, silver carboxylate, silver lactate, silver oxalate and their derivatives. It is not specially defined to the compounds above, but silver oxide or silver carbonate is preferably used because of its reactivity or after treatment in the present invention.

In the formula 2 to 4, $R_1$, $R_2$, $R_3$, $R_4$, $R_5$ and $R_6$ are same or different mutually. They are substituted groups selected from the group consisting of hydrogen, C1-C30 of aliphatic or cycloaliphatic alkyl group or aryl or aralkyl group, alkyl and aryl group substituted with functional group, heterocyclic compound, polymer compound and their derivatives, but it is not specially defined to the compounds above. For example, they can be selected from the group consisting of hydrogen, methyl, ethyl, propyl, isopropyl, butyl, isobutyl, amyl, hexyl, ethylhexyl, heptyl, octyl, isooctyl, nonyl, decyl, dodecyl, hexadecyl, octadecyl, docodecyl, cyclopropyl, cyclopentyl, cyclohexyl, allyl, hydroxy, methoxy, hydroxyethyl, methoxyethyl, 2-hydroxy propyl, methoxypropyl, cyanoethyl, ethoxy, buthoxy, hexyloxy, methoxyethoxyethyl, methoxyethoxyethoxyethyl, hexamethyleneimine, morpholine, piperidine, piperazine, ethylenediamine, propylenediamine, hexamethylenediamine, triethylenediamine, pyrrol, imidazol, pyridine, carboxymethyl, trimethoxysilylpropyl, triethoxysilylpropyl, phenyl, methoxyphenyl, cyanophenyl, phenoxy, tolyl, benzyl and their derivatives, and polymer compounds such as polyallylamine or polyethyleneamine and their derivatives, but it is not specially defined to the compounds above. As the concrete compounds, for example, they are one or more than two mixture selected from the group consisting of ammonium carbamate, ammonium carbonate, ammonium bicarbonate, ethylammonium ethylcarbamate, isopropylammonium isopropylcarbamate, n-butylammonium n-butylcarbamate, isobutylammonium isobutylcarbamate, t-butylammonium t-butylcarbamate, 2-ethylhexylammonium 2-ethylhexylcarbamate, octadecylammonium octadecylcarbamate, 2-methoxyethylammonium 2-methoxyethylcarbamate, 2-cyanoethylammonium 2-cyanoethylcarbamate, dibutylammonium dibutylcarbamate, dioctadecylammonium dioctadecylcarbamate, methyldecylammonium methyldecylcarbamate, hexamethyleneimineammonium hexamethyleneiminecarbamate, morpholinium morpholinecarbamate, pyridinium ethylhexylcarbamate, triethylenediaminium isopropylbicarbamate, benzylammonium benzylcarbamate, triethoxysilylpropylammonium triethoxysilylpropylcarbamate, ethylammonium ethylcarbonate, isopropylammonium isopropylcarbonate, isopropylammonium bicarbonate, n-butylammonium n-butylcarbonate, isobutylammonium isobutylcarbonate, t-butylammonium t-butylcarbonate, t-butylammonium bicarbonate, 2-ethylhexylammonium 2-ethylhexylcarbonate, 2-ethylhexylammonium bicarbonate, 2-methoxyethylammonium 2-methoxyethylcarbonate, 2-methoxyethylammonium bicarbonate, 2-cyanoethylammonium 2-cyanoethylcarbonate, 2-cyanoethylammonium bicarbonate, octadecylammonium octadecylcarbonate, dibutylammonium dibutylcarbonate, dioctadecylammonium dioctadecylcarbonate, dioctadecylammonium bicarbonate, methyldecylammonium methyldecylcarbonate, hexamethyleneimineammonium hexamethyleneiminecarbonate, morpholineammonium morpholinecarbonate, benzylammonium benzylcarbonate, triethoxysilylpropylammonium triethoxysilylpropylcarbonate, pyridinium bicarbonate, triethylenediaminium isopropylcarbonate, triethylenediaminium bicarbonate and their derivatives.

On the other hand, it doesn't necessarily have to restrict the kind of ammonium carbamate or ammonium carbonate based compounds and their manufacturing methods. For example, U.S. Pat. No. 4,542,214 (Sep. 17, 1985) discloses that ammonium carbamate based compounds can be prepared from primary amine, secondary amine, tertiary amine or at least more than one of these compounds and carbon dioxide. Ammonium carbonate based compounds can be obtained if 0.5 mole of water is added per one mole of amine, and ammonium bicarbonate based compounds can be obtained if more than one mole of water is added. In case they are made with or without any specific solvent in the condition of pressure or ambient pressure, the followings are to be used: water, alcohols such as methanol, ethanol, isopropanol and butanol, glycols such as ethyleneglycol and glycerine, acetates such as ethyl acetate, butyl acetate and carbitol acetate, ethers such as diethyl ether, tetrahydrofuran and dioxane, ketones such as methyl ethyl ketone and acetone, hydrocarbons such as hexane and heptane, aromatic compounds such as benzene and toluene, halogen substituted solvents such as chloroform, methylene chloride and carbontetrachloride, or mixed solvents of the above. As for carbon dioxide, it can be used as bubbled ones in the vapor phase or as solid dry ices. It can react in the supercritical condition, too. To prepare ammonium carbamate or ammonium carbonate derivatives that are used in the present invention, it is fine to use any methods including the above ones, if the final material structure is identical. In other words, it doesn't necessarily have to put restrictions on solvents, reaction temperature, concentration, catalyst, etc. for preparation and its yield.

Organic silver complexes can be manufactured by reaction between ammonium carbamate or ammonium carbonate based compounds and silver compounds. For instance, the preparation takes at least more than one silver compound as shown in Formula 1 and at least more than one ammonium carbamate or ammonium carbonate derivatives as shown in Formula 2 to 4 and the complex of these, which react by themselves without solvents in the nitrogen condition of pressure or ambient pressure. In case solvents are used, the followings can be used: water, alcohols such as methanol, ethanol, isopropanol and butanol, glycols such as ethyleneglycol and glycerine, acetates such as ethyl acetate, butyl acetate and carbitol acetate, ethers such as diethyl ether, tetrahydrofuran and dioxane, ketones such as methyl ethyl ketone and acetone, hydrocarbons such as hexane and heptane, aromatic compounds such as benzene and toluene, and halogen substituted solvents such as chloroform, methylene chloride, carbontetrachloride, or mixed solvents of the above.

To prepare silver complexes that are used in the present invention, besides the above methods, it can be manufactured by preparing a mixed solution of silver compound (Formula 1) and more than one amine compound and then making it react with carbon dioxide. Like above, it can react either with or without solvents in the nitrogen condition of pressure or ambient pressure. However, it is fine to use any methods if the final material structure is identical. In other words, it doesn't necessarily have to put restrictions on solvents, reaction temperature, concentration, catalyst, etc. for preparation and its yield.

The manufacturing method of the silver complexes according to the present invention is disclosed in Korean Patent Application No. 10-2006-0011083 by the inventors of the present invention. It has the structure of Formula 5 below.

$$Ag[A]_m \qquad \text{[Formula 5]}$$

[A is the compound of Formula 2 to 4, and m ranges in 0.5~1.5.]

The antibacterial composition containing silver complexes of the present invention is well dissolved in the solvents such as water and alcohols or the complex of these, so it can be easily applied to coating or printing processes and it is greatly stable when stored. The above solvent is one or more than two mixture selected from the group consisting of water, methanol, ethanol, isopropanol, butanol, ethyleneglycol, glycerine, ethyl acetate, butyl acetate, carbitol acetate, diethyl ether, tetrahydrofuran, dioxane, methyl ethyl ketone, acetone, hexane, heptane, benzen, toluene, chloroform, methylene chloride, carbontetrachloride or the mixed solvents of the above, but it doesn't necessarily have to put restrictions on the rate of the silver complexes and the solvents. That is, its range depends on the disinfection object or subject disinfected materials. Generally, it is preferable that the concentration of the silver complexes ranges 1~1000 ppm, more preferably, 3~100 ppm.

The antibacterial composition of the present invention has excellent stability and solubility, so its antibacterial treatment can be applicable to various products through coating processes such as spin coating, roll coating, spray coating, dip coating, flow coating, doctor blade coating, dispensing, inkjet printing, off-set printing, screen printing, pad printing, Gravure printing, Flexo printing and Riso printing, or padding.

As for textiles, they can be treated through padding or spraying using the antibacterial composition above; plastics, papers (wallpapers), floors can be thin film coated or directly printed for antibacterial treatment. Or they can be antibacterial treated in the manufacturing process respectively.

The antibacterial composition above can be applied to various products such as textiles, wallpapers, tableware, etc. for antibacterial treatment.

In case of textiles, the antibacterial composition above can remain through padding or spraying, after adsorption into the surface or inside of the textiles. The yarn, the material of the textiles, can be also treated in the manufacturing process. Particularly, it can be imbedded into the inside of the yarn after conjugate spinning in acryl or nylon polymers during the manufacturing process.

Also, generally in case of wallpapers, specific patterns are screen-printed on the rear sheet composed of woven fabrics or papers, or copperplate or Gravure printing is used. These wallpapers can be treated through being printed by the ink composition added with the antibacterial composition above or being coated with the antibacterial composition on one surface of finished wallpapers. Moreover, antibacterial woven fabrics or papers, which are the main materials of wallpapers, can be manufactured after the antibacterial composition is added during the manufacturing process.

Also, in case of ceramics such as tableware, they are antibacterial treated by adding the antibacterial composition to the glaze or spraying the antibacterial composition onto the manufactured ceramic products.

By adding or coating the antibacterial composition of the present invention during the manufacturing process or after completing the products, the antibacterial treatment for the products is possible. The order of antibacterial treatment process or methods can be different depending on the kind of the products.

The antibacterial-treated products undergo oxidation, reduction, heat process, infrared ray, ultraviolet, electronic beam or laser process. Especially by heat process, antibacterial formed articles with excellent durability and antibacterial power can be made. The above heat process ranges in temperature of 60~300° C., more desirably 80~150° C., in order to minimize the material change of the subject media.

DESCRIPTION OF DRAWINGS

FIG. 1 shows the photo of the cultivated state of the strain in Experimental Example 1 ((a) control sample, (b) Example 2, (c) Example 3, (d) Example 4, (e) Example 5, (f) Example 6).

FIG. 2 shows the photo of the cultivated state of the strain in Experimental Example 2 ((a) control sample, (b) Example 8, (c) Example 9).

FIG. 3 shows the photo of the cultivated state of the strain in Experimental Example 3 ((a) control sample, (b) Example 11, (c) Example 12).

FIG. 4 shows the photo of the cultivated state of the strain in Experimental Example 4 depending on the number of washing ((a) twice in a row, (b) four times in a row, (c) six times in a row, (d) ten times in a row).

FIG. 5 shows the TEM photo of the antibacterial processed cotton in Experimental Example 4.

FIG. 6 shows the photo of the cultivated state of the strain in Experimental Example 5 ((a) control sample, (b) Example 4).

MODE FOR INVENTION

Hereinafter, the present invention is described in more detail based on the following examples. But, these examples are not intended to limit the scope of the present invention.

EXAMPLE 1

2.97 g of isopropylammonium bicarbonate (24.51 mmol) was first dissolved in 10 ml of methanol within a 50 ml Schlenk flask equipped with an agitator, and 1.0 g of silver oxide (4.31 mmol) was added. It was observed that the color of the reacted solution was gradually changing from black slurry to transparent while the reaction was progressing. Two hours later, it was changed to the completely colorless and transparent solution, which indicates that the complex was created. By filtering this solution using the 0.45 μm membrane filter, silver oxide particles which didn't react were eliminated. Then, after the solvent was all eliminated under vacuum, 2.41 g of white solid-state silver complex (yield: 60.7%), which carried 39.8 wt % of silver contents versus the silver complex, was obtained. By adding distilled water to 1.26 g of said complex and dissolving it to make 500 g of total weight, the antibacterial composition containing 1000 ppm of silver was prepared.

EXAMPLE 2

For 3 g of the antibacterial composition containing 1000 ppm of silver prepared in Example 1, distilled water was added to make 1000 g of total weight, in order to prepare the antibacterial composition containing 3 ppm of silver.

EXAMPLE 3

For 5 g of the antibacterial composition containing 1000 ppm of silver prepared in Example 1, distilled water was added to make 1000 g of total weight, in order to prepare the antibacterial composition containing 5 ppm of silver.

EXAMPLE 4

For 10 g of the antibacterial composition containing 1000 ppm of silver prepared in Example 1, distilled water was added to make 1000 g of total weight, in order to prepare the antibacterial composition containing 10 ppm of silver.

EXAMPLE 5

For 30 g of the antibacterial composition containing 1000 ppm of silver prepared in Example 1, distilled water was added to make 1000 g of total weight, in order to prepare the antibacterial composition containing 30 ppm of silver.

EXAMPLE 6

For 100 g of the antibacterial composition containing 1000 ppm of silver prepared in Example 1, distilled water was added to make 1000 g of total weight, in order to prepare the antibacterial composition containing 100 ppm of silver.

EXAMPLE 7

32.5 g of 2-ethylhexylammonium 2-ethylhexylcarbamate (107.5 mmol), a viscous solution, was first dissolved in 100 ml of methanol within a 250 ml Schlenk flask equipped with an agitator and then reacted at room temperature after 10.0 g of silver oxide (43.1 mmol) was added. It was observed that the color was gradually changing from black slurry to light while the reaction was progressing. Two hours later, it was changed to the completely colorless and transparent solution, which indicates that the complex was created. By filtering this solution using the 0.45 μm membrane filter, silver oxide particles which didn't react were eliminated. Then, after the solvent was all eliminated under vacuum, 42.0 g of white solid-state silver complex (yield: 98.8%), which carried 21.9 wt % of silver contents versus the silver complex, was obtained. By adding ethanol to 4.57 g of said complex and dissolving it to make 1000 g of total weight, the antibacterial composition containing 1000 ppm of silver was prepared.

EXAMPLE 8

For 10 g of the antibacterial composition containing 1000 ppm of silver prepared in Example 7, ethanol was added to make 1000 g of total weight, in order to prepare the antibacterial composition containing 10 ppm of silver.

EXAMPLE 9

For 30 g of the antibacterial composition containing 1000 ppm of silver prepared in Example 7, ethanol was added to make 1000 g of total weight, in order to prepare the antibacterial composition containing 30 ppm of silver.

EXAMPLE 10

32.7 g of 2-ethylhexylammonium 2-ethylhexylcarbamate (108 mmol), a viscous solution, was first dissolved in 50 ml of methanol within a 50 ml Schlenk flask equipped with an agitator, and 10.0 g of silver carbonate (3.60 mmol) was added. It was observed that the color was gradually changing from yellow slurry to transparent while the reaction was progressing. Five hours later, it was changed to the completely transparent solution, which indicates that the complex was successfully created. By filtering this solution using the 0.45 μm membrane filter, silver carbonate particles which didn't react were eliminated. Then, after the solvent was all eliminated under vacuum, 41.4 g of white solid-state silver complex (yield: 96.9%), which carried 16.5 wt % of silver contents versus the silver complex, was obtained. By adding the solution prepared by distilled water and ethanol on a weight ratio of 7:3 to 6.06 g of said complex and dissolving it to make 1000 g of total weight, the antibacterial composition containing 1000 ppm of silver was prepared.

EXAMPLE 11

For 10 g of the antibacterial composition containing 1000 ppm of silver prepared in Example 10, the solution prepared by distilled water and ethanol on a weight ratio of 7:3 was added to make 1000 g of total weight, in order to prepare the antibacterial composition containing 10 ppm of silver.

EXAMPLE 12

For 30 g of the antibacterial composition containing 1000 ppm of silver prepared in Example 10, the solution prepared by distilled water and ethanol on a weight ratio of 7:3 was added to make 1000 g of total weight, in order to prepare the antibacterial composition containing 30 ppm of silver.

EXPERIMENTAL EXAMPLE 1

The antibacterial composition prepared in Example 2 to 6 above was padded on the cotton, and then heat-treated at 140° C. for 10 minutes for the experimental sample. To each experimental sample and control sample, $1.3 \times 10^5$ ea/ml of *Staphylococcus aureus* (ATCC 6538) was inoculated and then the bacteriostasis decrease rate was measured according to the KS K 0693:2001 method. The results are shown below in Table 1. Also, the cultivated state of the strain above is shown in FIG. 1.

TABLE 1

|  | Example 2 | Example 3 | Example 4 | Example 5 | Example 6 |
|---|---|---|---|---|---|
| Silver content (ppm) | 3 | 5 | 10 | 30 | 100 |
| Bacteriostasis decrease rate (%) *staphylococcus aureus* | 99.9 | 99.9 | 99.9 | 99.9 | 99.9 |

In FIG. 1, which shows the cultivated state of the strain, FIG. 1a shows the cultivated state of the strain of the control sample, and FIG. 1b to 1f show the cultivated state of the strain in the experimental sample of cotton, in which silver complexes prepared in Example 2 to 6 were treated. From the above in both Table 1 and FIG. 1, it was found that the experimental sample of cotton, where silver complexes prepared in Example 2 to 6 were treated, has high antibacterial power with 99.9% of bacteriostasis decrease rate.

EXPERIMENTAL EXAMPLE 2

The antibacterial composition prepared in Example 8 and 9 above was padded on the cotton, and then heat-treated at 110° C. for 10 minutes for the experimental sample. To each experimental sample and control sample, $1.3 \times 10^5$ ea/ml of *Klebsiella pneumoniae* (ATCC 4352) was inoculated and then the bacteriostasis decrease rate was measured according to the KS K 0693:2001 method. The results are shown below in Table 2. Also, the cultivated state of the strain above is shown in FIG. 2.

TABLE 2

|  | Example 8 | Example 9 |
|---|---|---|
| Silver content (ppm) | 10 | 30 |
| Bacteriostasis decrease rate (%) Klebsiella pneumoniae | 99.9 | 99.9 |

In FIG. 2, which shows the cultivated state of the strain, FIG. 2a shows the cultivated state of the strain of the control sample, and FIGS. 2b and 2c show the cultivated state of the strain in the experimental sample of cotton, in which silver complexes prepared in Example 8 and 9 were treated.

From the above in both Table 2 and FIG. 2, it was found that the experimental sample of cotton, where silver complexes prepared in Example 8 and 9 were treated, has high antibacterial power with 99.9% of bacteriostasis decrease rate.

EXPERIMENTAL EXAMPLE 3

The antibacterial composition prepared in Example 11 and 12 above was respectively padded on the cotton, and then heat-treated at 120° C. for 10 minutes for the experimental sample. To each experimental sample and control sample, $1.3 \times 10^5$ ea/ml of Escherichia coli (ATCC 25922) was inoculated and then the bacteriostasis decrease rate was measured according to the KS K 0693:2001 method. The results are shown below in Table 3. Also, the cultivated state of the strain above is shown in FIG. 3.

TABLE 3

|  | Example 11 | Example 12 |
|---|---|---|
| Silver content (ppm) | 10 | 30 |
| Bacteriostasis decrease rate (%) Escherichia coli | 99.9 | 99.9 |

In FIG. 3, which shows the cultivated state of the strain, FIG. 3a shows the cultivated state of the strain of the control sample, and FIGS. 3b and 3c show the cultivated state of the strain in the experimental sample of cotton, in which silver complexes prepared in Example 11 and 12 were treated.

From the above in both Table 2 and FIG. 3, it was found that the experimental sample of cotton, where silver complexes prepared in Example 11 and 12 were treated, has high antibacterial power with 99.9% of bacteriostasis decrease rate.

EXPERIMENTAL EXAMPLE 4

The antibacterial composition prepared in Example 5 above was padded on the cotton, and then heat-treated at 140° C. for 10 minutes for the experimental sample. To the experimental samples, which were washed respectively twice, four times, six times, and ten times in a row, $1.3 \times 10^5$ ea/ml of Staphylococcus aureus (ATCC 6538) was inoculated and then the bacteriostasis decrease rate was measured according to the KS K 0693:2001 method. The results are shown below in Table 4. Also, the cultivated state of the strain above is shown in FIG. 4.

TABLE 4

|  | After washing twice in a row | After washing four times in a row | After washing six times in a row | After washing ten times in a row |
|---|---|---|---|---|
| Bacteriostasis decrease rate (%) staphylococcus aureus | 99.9 | 99.9 | 99.9 | 99.9 |

In FIG. 4, which shows the cultivated state of the strain, FIG. 4a to 4d show the cultivated state of the strain in the experimental samples of cotton, which were treated with the antibacterial composition containing silver complexes prepared in Example 5 and then respectively washed twice, four times, six times, and ten times in a row.

From the above in both Table 4 and FIG. 4, it was found that when the cotton, which is treated with the antibacterial composition containing silver complex prepared in Example 5, is washed several times, it has high antibacterial power with 99.9% of bacteriostasis decrease rate. This is because silver particles remain after adsorption into the surface of the cotton as well as inside of it, as shown in the TEM photo of FIG. 5.

EXPERIMENTAL EXAMPLE 5

The antibacterial composition prepared in Example 4 above was padded on the PET non-woven fabric, and then heat-treated at 110° C. for 10 minutes for the experimental sample. To each experimental sample and control sample, $1.2 \times 10^5$ ea/ml of Staphylococcus aureus (ATCC 6538) was inoculated and then the bacteriostasis decrease rate was measured according to the KS K 0693:2001 method. The results are shown below in Table 5. Also, the cultivated state of the strain above is shown in FIG. 6.

TABLE 5

|  | Example 4 |
|---|---|
| Silver content (ppm) | 10 |
| Bacteriostasis decrease rate (%) staphylococcus aureus | 99.2 |

In FIG. 6, which shows the cultivated state of the strain, FIG. 6a shows the cultivated state of the strain of the control sample, and FIG. 6b shows the cultivated state of the strain in the experimental sample of PET non-woven fabric, which was treated with the antibacterial composition containing silver complex prepared in Example 4.

From the above in both Table 5 and FIG. 6, it was found that PET non-woven fabric, which is treated with the antibacterial composition containing silver complex prepared in Example 4 has high antibacterial power with 99.2% of bacteriostasis decrease rate.

INDUSTRIAL APPLICABILITY

The antibacterial composition containing silver complexes according to the present invention is economical, not wearing off due to washing, cleaning, rubbing, etc., firmly combined to improve durability and antibacterial effect, and applicable to various products due to great solubility and stability.

The invention claimed is:

1. An antibacterial composition containing one or more silver complexes that are obtained by the reaction between one or more silver compounds of Formula 1 and one or more ammonium carbamate or ammonium carbonate based compounds selected from Formula 2 to 4:

$Ag_nX$   Formula 1

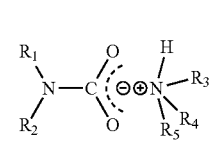 or 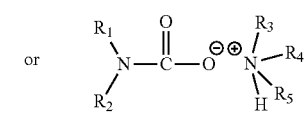

Formula 2

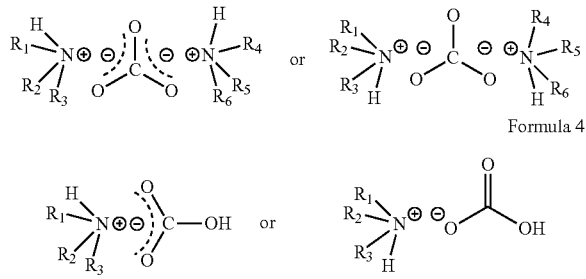

In the formula above,

X is a substituted group selected from the group consisting of oxygen, sulfur, halogen, cyano, cyanate, carbonate, nitrate, nitrite, sulfate, phosphate, thiocyanate, chlorate, perchlorate, tetrafluoro borate, acetylacetonate, carboxylate and their derivatives, n is an integer of 1-4, $R_1$ to $R_6$ are substituted groups independently selected from the group consisting of hydrogen, C1-C30 of aliphatic or cycloaliphatic alkyl group or aryl or aralkyl group, alkyl and aryl group substituted with functional group, heterocyclic compound, polymer compound and their derivatives, and $R_1$ to $R_6$ are not all hydrogen.

2. The antibacterial composition of claim 1, wherein said silver complex has the structure of Formula 5:

A is the compound of Formula 2 to 4, and m ranges in 0.5-1.5.

3. The antibacterial composition of claim 1, wherein $R_1$ to $R_6$ are independently selected from the group consisting of hydrogen, methyl, ethyl, propyl, isopropyl, butyl, isobutyl, amyl, hexyl, ethylhexyl, heptyl, octyl, isooctyl, nonyl, decyl, dodecyl, hexadecyl, octadecyl, docodecyl, cyclopropyl, cyclopentyl, cyclohexyl, allyl, hydroxy, methoxy, methoxyethyl, methoxypropyl, cyanoethyl, ethoxy, butoxy, hexyloxy, methoxyethoxyethyl, methoxyethoxyethoxyethyl, hexamethyleneimine, morpholine, piperidine, piperazine, ethylenediamine, propylenediamine, hexamethylenediamine, triethylenediamine, pyrrol, imidazol, pyridine, carboxymethyl, trimethoxysilylpropyl, triethoxysilylpropyl, phenyl, methoxyphenyl, cyanophenyl, phenoxy, tolyl, benzyl, polyallylamine, polyethyleneamine and their derivatives, and $R_1$ to $R_6$ are not all hydrogen.

4. The antibacterial composition of claim 1, wherein said silver compound is one or more selected from the group consisting of silver oxide, silver thiocyanate, silver cyanide, silver cyanate, silver carbonate, silver nitrate, silver nitrite, silver sulfate, silver phosphate, silver perchlorate, silver tetrafluoro borate, silver acetylacetonate, silver carboxylate, silver lactate, silver oxalate and their derivatives.

5. The antibacterial composition of claim 1, wherein said ammonium carbamate or ammonium carbonate based compounds are one or more selected from the group consisting of ethylammonium ethylcarbamate, isopropylammonium isopropylcarbamate, n-butylammonium n-butylcarbamate, isobutylammonium isobutylcarbamate, t-butylammonium t-butylcarbamate, 2-ethylhexylammonium 2-ethylhexylcarbamate, octadecylammonium octadecylcarbamate, 2-methoxyethylammonium 2-methoxyethylcarbamate, 2-cyanoethylammonium 2-cyanoethylcarbamate, dibutylammonium dibutylcarbamate, dioctadecylammonium dioctadecylcarbamate, methyldecylammonium methyldecylcarbamate, hexamethyleneimineammonium hexamethyleneiminecarbamate, morpholinium morpholinecarbamate, pyridinium ethylhexylcarbamate, triethylenediaminium isopropylbicarbamate, benzylammonium benzylcarbamate, triethoxysilylpropylammonium triethoxysilylpropylcarbamate, ethylammonium ethylcarbonate, isopropylammonium isopropylcarbonate, isopropylammonium bicarbonate, n-butylammonium n-butylcarbonate, isobutylammonium isobutylcarbonate, t-butylammonium t-butylcarbonate, t-butylammonium bicarbonate, 2-ethylhexylammonium 2-ethylhexylcarbonate, 2-ethylhexylammonium bicarbonate, 2-methoxyethylammonium 2-methoxyethylcarbonate, 2-methoxyethylammonium bicarbonate, 2-cyanoethylammonium 2-cyanoethylcarbonate, 2-cyanoethylammonium bicarbonate, octadecylammonium octadecylcarbonate, dibutylammonium dibutylcarbonate, dioctadecylammonium dioctadecylcarbonate, dioctadecylammonium bicarbonate, methyldecylammonium methyldecylcarbonate, hexamethyleneimineammonium hexamethyleneiminecarbonate, morpholineammonium morpholinecarbonate, benzylammonium benzylcarbonate, triethoxysilylpropylammonium triethoxysilylpropylcarbonate, pyridinium bicarbonate, triethylenediaminium isopropylcarbonate, triethylenediaminium bicarbonate and their derivatives.

6. The antibacterial composition of claim 1, wherein said composition further comprises solvent.

7. The antibacterial composition of claim 6, wherein said solvent is one or more selected from the group consisting of water, alcohol, glycol, acetate, ether, ketone, aliphatic hydrocarbon, aromatic hydrocarbon and halogen substituted hydrocarbon solvent.

8. The antibacterial composition of claim 7, wherein said solvent is one or more selected from the group consisting of water, methanol, ethanol, isopropanol, butanol, ethyleneglycol, glycerine, ethyl acetate, butyl acetate, carbitol acetate, diethyl ether, tetrahydrofuran, dioxane, methyl ethyl ketone, acetone, hexane, heptane, benzene, toluene, chloroform, methylene chloride, carbontetrachloride or mixture thereof.

9. The antibacterial composition of claim 1, wherein the concentration of said silver complexes ranges from 1-1000 ppm.

10. A method of antibacterial treatment comprising applying the antibacterial composition of claim 1 by the method selected from the group consisting of spin coating, roll coating, spray coating, dip coating, flow coating, doctor blade coating, dispensing, inkjet printing, off-set printing, screen printing, pad printing, Gravure printing, Flexo printing or Riso printing.

11. The method of claim 10, further comprising oxidation, reduction, heat process, infrared ray, ultraviolet, electronic beam or laser process after said application.

12. The antibacterial treatment method of claim 11, wherein said heat process ranges in temperature of 60-300° C.

13. An antibacterial formed article treated by the antibacterial composition of claim 1.

* * * * *